(12) United States Patent
Penninger et al.

(10) Patent No.: US 9,883,972 B2
(45) Date of Patent: Feb. 6, 2018

(54) EYE PROTECTION GOGGLES

(71) Applicant: LASERVISION GmbH & Co. KG, Fürth (DE)

(72) Inventors: Christian Penninger, Nürnberg (DE); Lars Horn, Hamburg (DE); Thomas Fröhlich, Lauf an der Pegnitz (DE)

(73) Assignee: LASERVISION GMBH & CO. KG, Fürth (DE)

( * ) Notice: Subject to any disclaimer, the term of this patent is extended or adjusted under 35 U.S.C. 154(b) by 0 days.

(21) Appl. No.: 14/926,157

(22) Filed: Oct. 29, 2015

(65) Prior Publication Data
US 2016/0120702 A1  May 5, 2016

(30) Foreign Application Priority Data
Oct. 31, 2014  (DE) .......................... 10 2014 222 329

(51) Int. Cl.
*A61F 9/02* (2006.01)
*A61F 9/04* (2006.01)

(52) U.S. Cl.
CPC ............... *A61F 9/04* (2013.01); *A61F 9/022* (2013.01); *A61F 9/025* (2013.01); *A61F 9/027* (2013.01)

(58) Field of Classification Search
CPC .. A61F 9/02; A61F 9/022; A61F 9/025; A61F 9/04
USPC .............. 128/857, 858; 2/15, 426, 431, 434, 2/440–444
See application file for complete search history.

(56) References Cited

U.S. PATENT DOCUMENTS

| | | | |
|---|---|---|---|
| 5,918,600 A | 7/1999 | Durette | |
| 5,927,281 A | 7/1999 | Monteleone et al. | |
| 6,081,934 A | 7/2000 | Stefanovsky et al. | |
| 7,188,625 B2 * | 3/2007 | Durette | A61F 9/04 128/858 |
| 8,667,612 B2 * | 3/2014 | Frohlich | A61F 9/04 2/15 |
| 2007/0130674 A1 | 6/2007 | Beyer | |

(Continued)

FOREIGN PATENT DOCUMENTS

DE  10 2005 058 888 B3  3/2007
FR       1393280 A  3/1965

*Primary Examiner* — Keri J Nelson
(74) *Attorney, Agent, or Firm* — Browdy and Neimark, PLLC (57) ABSTRACT

Eye protection goggles for protecting a person undergoing treatment from electromagnetic radiation comprise two eye protection caps. Each eye protection cap comprises a basic protective body with a free edge for protecting from electromagnetic radiation and a cover protective body detachable from the respective basic protective body for protecting from frontal electromagnetic radiation. The free edge is designed for placing on the face of the person undergoing treatment. The eye protection goggles also have a connecting web connecting the cover protective bodies. The cover protective bodies are connected non-detachably in one piece to one another. The connecting web comprises an in particular rectangular first cross section (2a) extending longitudinally in a width direction of the eye protective goggles for displacing the connecting web relative to the eye protection caps essentially perpendicular to a line of vision of the eye protective goggles in a vertical direction thereof.

27 Claims, 4 Drawing Sheets (56) References Cited

U.S. PATENT DOCUMENTS

2008/0072366 A1* 3/2008 Fukasawa ............ A63B 33/002
                                                    2/445
2009/0031483 A1* 2/2009 Wallerberger ......... A42B 3/328
                                                    2/421

* cited by examiner

EYE PROTECTION GOGGLES

CROSS-REFERENCES TO RELATED APPLICATIONS

This application claims the priority of German Patent Application, Serial No. 10 2014 222 329.6, filed Oct. 31, 2014, pursuant to 35 U.S.C. 119(a)-(d), the content of which is incorporated herein by reference in its entirety as if fully set forth herein.

FIELD OF THE INVENTION

The invention relates to eye protection goggles for protecting a person undergoing treatment from electromagnetic radiation, in particular laser radiation. Furthermore, the invention relates to an arrangement as a component of such eye protection goggles.

BACKGROUND OF THE INVENTION

Medical laser treatments can be used on people to treat wrinkles or skin anomalies, such as age spots and warts. For this the eyes of the person undergoing the treatment and the eyes of the person performing the treatment need to be protected from the effects of laser radiation.

To protect the eyes of the person undergoing treatment it is known to use eyeball goggles for example which comprise two half shells for covering the eyes. The half shells are joined together by means of a connecting web and are held on the head of the person undergoing treatment by a headband. Generic eyeball goggles are known for example from DE 10 2005 058 888 B3. A disadvantage of such eyeball goggles is that their protective effect is often inadequate. Furthermore, people often find them uncomfortable to wear.

Eye protection goggles for protecting a person undergoing laser treatment in the face are known from U.S. Pat. No. 6,081,934. The eye protection goggles comprise two eye protection caps. Each eye protection cap carries a circumferential mounting flange which is designed to carry a circumferential skin sealing element. The skin sealing element consists of a soft, flexible material such as rubber. Furthermore, a bridge connecting component is arranged on each eye protection cap. An adjustable bridge band is connected to the bridge connection components and connects the eye protection caps. These eye protection goggles are expensive in their production. Furthermore, the bridge band is generally disturbing in a laser treatment in the face.

U.S. Pat. No. 5,918,600 discloses an eye protection device with two separate eye shields which block laser radiation. Each eye shield carries a hook, to which an end of a nose bridge spring can be attached.

SUMMARY OF THE INVENTION

An underlying objective of the invention is to provide eye protection goggles which on the one hand provide a particularly high level of protection from electromagnetic radiation and on the other hand are extremely comfortable to wear. In addition, a corresponding arrangement is also provided as a component of the eye protection goggles.

Said object is achieved according to the invention by protection goggles for protecting a person undergoing treatment from electromagnetic radiation, in particular from laser radiation, comprising two eye protection caps, wherein each eye protection cap comprises a basic protective body for protecting from electromagnetic radiation, wherein each basic protective body has a free edge being designed for placing on the face of the person undergoing treatment, comprises a cover protective body for protecting from frontal electromagnetic radiation, wherein each cover protective body being detachably connected to the respective basic protective body, and spatially delimits an inner chamber, and a connecting web connecting the cover protective bodies with each other, wherein the cover protective bodies and the connecting web are connected non-detachably in one piece with each other, wherein the connecting web comprises at least adjacent to the eye protection caps a first cross section, extending longitudinally in a width direction of the eye protective goggles, for displacing the connecting web relative to the eye protection caps essentially perpendicular to a line of vision of the eye protective goggles in a vertical direction thereof.

The object of the invention is further achieved by an arrangement as a component of eye protective goggles according to the invention, comprising two cover protective bodies which are connectable detachably to two basic protective bodies to form two eye protection caps, and a connecting web in connection with the cover protective bodies, wherein the cover protective bodies and the connecting web are connected non-detachably in one piece, wherein the connecting web comprises at least adjacent to the eye protection caps a first cross section, extending longitudinally in a width direction of the eye protective goggles, for displacing the connecting web relative to the eye protection caps essentially perpendicular to a line of vision of the eye protective goggles in a vertical direction thereof.

The core of the invention is that the eye protection caps for covering the eyes of the person undergoing treatment each comprise a basic protective body and a cover protective body, which in the assembled state of the respective eye protection cap are connected in a detachable manner. The eye protection caps thus consist of multiple parts, in particular two parts. Thus it is possible to clean the eye protection caps particularly thoroughly. Furthermore, the protective bodies can be adapted specifically to the respective requirements, in particular with regard to their protective effect and/or wearing comfort.

The non-detachable, one-piece connection between the cover protective body and the connecting web results in a secure connection between the same. The one-piece connection between the cover protective bodies and the connecting web enables a particularly simple and inexpensive production of the latter. It is an advantage if the cover protective body and the connecting web are made from the same material.

In the eye protection goggles according to the invention the connecting web can be moved particularly easily and specifically, in order in particular to obtain unrestricted access to the area to be treated of the person undergoing treatment.

Preferably, each basic protective body is shell or cap-like. More preferably, each basic protective body is designed as a hollow moulded body. The basic protective bodies are preferably metal-free or made from a disinfectable material, which is suitable for placing in an autoclave in particular.

It is an advantage, if each basic protective body has a side wall which is preferably closed in circumferential direction. The side wall provides particular protection from lateral electromagnetic radiation.

It is preferable, if each basic protective body has a cover. The cover conveniently connects at an end area with the respective side wall and seals the basic protective body on one side. It is thus arranged preferably essentially opposite the respective free edge on the respective side wall. In particular, the cover provides protection from frontal electromagnetic radiation. The side wall and the cover of each eye protection cap are preferably in one piece or connected in one piece. It is advantageous if the latter are made from the same material.

Conveniently, an inner chamber is delimited spatially laterally outwards by each basic protective body. It is advantageous if the inner chamber tapers at least partly in a line of vision of the eye protection goggles. The inner chambers are preferably open or accessible via face openings.

It is advantageous if each basic protective body extends longitudinally in a width direction of the eye protection goggles, i.e. in the direction of the distance between the eyes of the person undergoing treatment.

It is an advantage if each cover protective body is designed to be plate-like or platelet-like. The cover protective bodies are preferably metal-free. Conveniently, each cover protective body in an assembled state of the eye protection goggles is arranged externally adjacent to the respective cover. By means of each cover protective body the protection from electromagnetic radiation can be improved or increased further. The cover protective bodies in particular provide additional protection from frontal electromagnetic radiation. Conveniently they form additional protective bodies.

The protective effect of the eye protection goggles or the eye protection caps is comparable with metal-based eye protection goggles and thus much greater than that of flat adhesive pads.

The eye protection caps are preferably designed as hollow moulded bodies. They are preferably not transparent. The eye protection caps are preferably metal-free and made from a material which can be disinfected and in particular can be placed in an autoclave.

The connecting web holds the eye protection caps together. It is designed advantageously in the form of a bridge.

It is preferable, if the eye protection caps can be secured locally by a head holding device to the head of the person undergoing treatment. The head holding device can be arranged directly or indirectly on the eye protection caps. It is designed for example in the form of a headband, strap arrangement or the like. It can be designed in one piece or in multiple parts.

It is an advantage, if the arrangement according to claim according to the invention is designed in one part or piece. It is preferably made from one material.

The eye protection goggles, in which the basic protective bodies are made from a first material and the cover protective bodies are made from a second material different from the first material, in particular in terms of hardness and/or protective effect, meet the requirements for modern eye protection goggles in a simple manner. They can be adjusted particularly effectively for example in terms of hardness and/or (laser) protection.

Flexible basic protective bodies made in particular of silicone can be adjusted particularly easily to the face or the eye areas of the person undergoing treatment. It is thus possible to prevent, in a particularly reliable manner, gaps forming between the respective basic protective body and the face of the person undergoing treatment, if the eye protection goggles are put on correctly. These gaps are dangerous as electromagnetic radiation can pass through them to the eyes of the person undergoing treatment without any restrictions. The flexible configuration of the basic protective bodies, which when in use are placed on the face of the person undergoing treatment, results in an extremely high degree of wearing comfort.

According to the invention the cover protective bodies and/or the connecting web is/are essentially dimensionally stable or rigid and is/are made in particular from thermoplastic material, in particular polyoxymethylene. To a certain extent in particular the connecting web can be deformed manually, so that for example the distance of the eye protection caps from one another can be altered. Separate joints, hinges or the like are not necessary for this. The eye protection caps can thus be adjusted easily to the eyes of the person undergoing treatment and/or to the distance of the eyes from one another.

By means of the configuration, in which each cover protective body is connected detachably to the associated basic protective body in a positive locking and/or force locking manner, a particularly secure and gap-free connection can be achieved between the cover protective body and the basic protective body. A connection of this kind can be produced easily and is also releasable.

It is an advantage if the at least one positive locking means is designed to be fully peripheral and is closed in circumferential direction. The groove is preferably rectangular in cross section. Preferably it is open laterally outwardly. The at least one counter positive locking means is conveniently completely peripheral or closed in circumferential direction. It is preferably rectangular in cross section. Conveniently, the at least one counter positive locking means engages externally from the side into the at least one positive locking means. Alternatively, a different or reverse arrangement is possible.

The configuration, in which the connecting web can be displaced at least partly relative to the eye protection caps essentially perpendicular to a line of vision of the eye protective goggles in a vertical direction thereof, allows the essentially unrestricted treatment of the person undergoing treatment by the person performing the treatment. It is thus possible to move the connecting web so that it allows free access to the area of the person to be treated that needs treatment. If for example the forehead of the person requires treatment, the connecting web is moved or pivoted out of the forehead area, for example into the nose area of the person to be treated. If for example the nose area of the person requires treatment the connecting web is moved or pivoted out of the nose area, for example into the forehead area of the person to be treated. It is an advantage if the connecting web can be moved or pivoted into at least two stabile positions. Alternatively, the connecting web can be moved continuously. According to a preferred embodiment the connecting web can be moved essentially as a whole. Alternatively, it can be moved only in part, advantageously in a central area.

The configuration, in which the connecting web spaced apart from the eye protection caps has in particular a rectangular second cross section extending longitudinally in a vertical direction of the eye protective goggles for changing the distance between the eye protection caps, results in eye protection goggles, which can be adjusted particularly easily to the person to be treated and the distance between their eyes. Said eye protection goggles are particularly comfortable and extremely secure.

The eye protection goggles, in which the connecting web extends at least partly in a vertical direction of the eye protective goggles and the eye protective goggles can be worn in a first position and a second head position rotated by 180° relative to the first position, provide the person performing the treatment with good access to the areas to be treated of the person undergoing treatment. Depending on the wearing position of the eye protection goggles the connecting web preferably extends either in a first vertical direction of the eye protection goggles or in a second vertical direction opposite the first vertical direction. Preferably, in this embodiment the connecting web cannot be moved relative to the eye protection caps.

The configuration, in which on each cover protective body a coupling body for holding a head holding device is arranged, which is in particular essentially dimensionally stable and in particular projects outwards laterally, in particular for detachably holding a head holding device, results in eye protection goggles, which can be fixed in place particularly well on the person to be treated. It is an advantage, if each coupling body is bowed or curved. Conveniently, a headband can be mounted in each coupling body for encompassing the head of the person to be treated.

The configuration, in which the cover protective bodies and the coupling bodies are joined non-detachably, preferably forming one piece, results in a secure connection between the cover protective body and the assigned coupling body. It is an advantage, if the cover protective body and the associated coupling body are made from the same material.

The configuration, in which each coupling body at least adjacent to the eye protection caps has in particular a rectangular third cross section extending longitudinally in width direction of the eye protective goggles for displacing the coupling bodies relative to the eye protection caps essentially perpendicular to a line of vision of the eye protective goggles in a vertical direction thereof, enables a particularly simple and specific adjustment of the coupling body in a vertical direction. The eye protection goggles can thus be adjusted extremely well to the person undergoing treatment.

In the following a preferred embodiment of the invention is described by way of example with reference to the accompanying drawings.

DESCRIPTION OF THE PREFERRED EMBODIMENT

Figure 6:
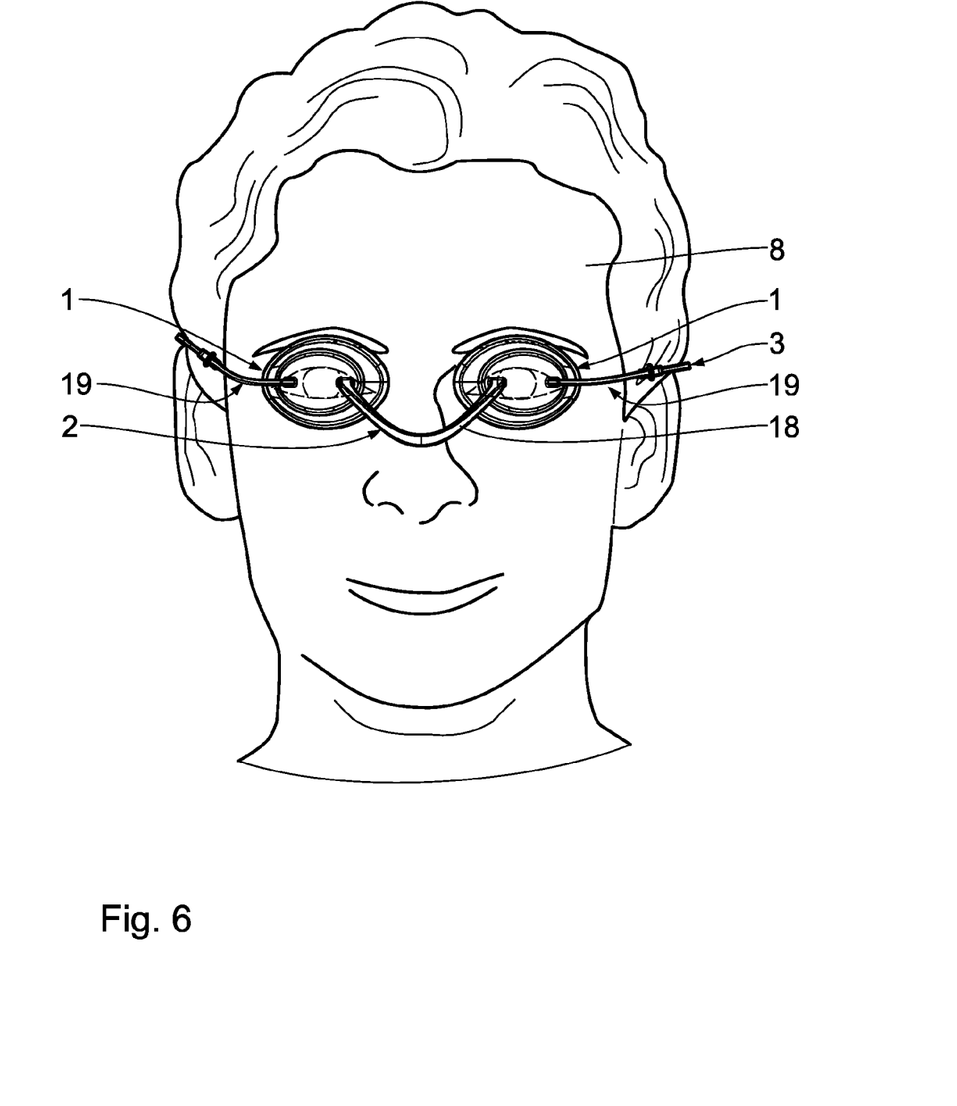
FIG. 6 shows the assembled eye protection goggles shown in FIG. 2 when being worn, wherein the connecting web is in a lower position, different from FIG. 3.

Eye protection goggles or eyeball goggles comprise two eye protection caps 1, a connecting web 2 connecting the eye protection caps 1 and a headband 3 connected to the eye protection caps 1. The eye protection goggles are designed to be symmetrical relative to a plane of symmetry E, which extends centrally between the eye protection caps 1. When the eye protection goggles are worn correctly as shown in FIG. 6 the eye protection caps 1 completely cover both eyes of the person to be treated 8. A separate eye protection cap 1 is provided for each eye.

As the eye protection caps 1 are identical in design, in the following reference is made to only one eye protection cap 1.

Each eye protection cap 1 comprises a basic protective body 4 and a cover protective body 5 which can be connected detachably to said basic protective body 4. The basic protective bodies 4 are essentially flexible, whereas the cover protective bodies 5 are designed to be essentially dimensionally stable. In the assembled state of the eye protection caps 1 each cover protective body 5 is connected detachably to the assigned basic protective body 4 in a positive locking manner.

Each basic protective body 4 has a peripherally closed side wall 6 with a foot-side, free edge 7 for placing on the face of the person to be treated 8. Spaced apart from the respective free edge 7 each basic protective body 4 has a cover 9, which closes the basic protective body 4 in a line of vision 10 of the eye protection goggles. The covers 9 are designed to be plate-like respectively and extend essentially perpendicular to the line of vision 10.

Opposite the free edges 7 on each side wall 6 a positive locking web 11 is arranged which is closed peripherally and projects inwardly from the respective side wall 6.

The positive locking web 11, the side wall 6 and the cover 9 are joined together in one piece with the respective eye protection cap 1. They are made from the same material, preferably silicone. By means of the side wall 6 and the cover 9 in each eye protection cap 1 respectively an inner chamber 12 is spatially delimited, which is preferably circular, elliptical or oval in cross section.

Each cover protective body 5 comprises a peripherally closed positive locking groove 1, which is designed to be open laterally to the outside and to be complementary to the positive locking web 11. Each cover protective body 5 has adjacent to the respective positive locking groove 13 an outer laterally outwardly projecting overhang 14, which is designed to be peripherally closed and delimits the respective positive locking groove 13 in the line of vision 10.

The connecting web 2 is connected in one piece to the cover protective bodies 5. It is curved in an arc and connects to the outer surface 15 of the respective cover protective bodies 5. The connecting web 2 in particular connects to a laterally inner area of the respective cover protective body 5. Adjacent to the respective cover protective body 5 it has a rectangular first cross section 2a extending longitudinally in a width direction 16 of the eye protection goggles, i.e. in a direction of the distance between the eyes of the person to be treated. The connecting web 2 has in the width direction 16 a width B and perpendicular thereto in a vertical direction 17 of the eye protection goggles a height H. t: $1.2 \leq B/H \leq 5$, more preferably $1.8 \leq B/H \leq 4$.

Figure 2:
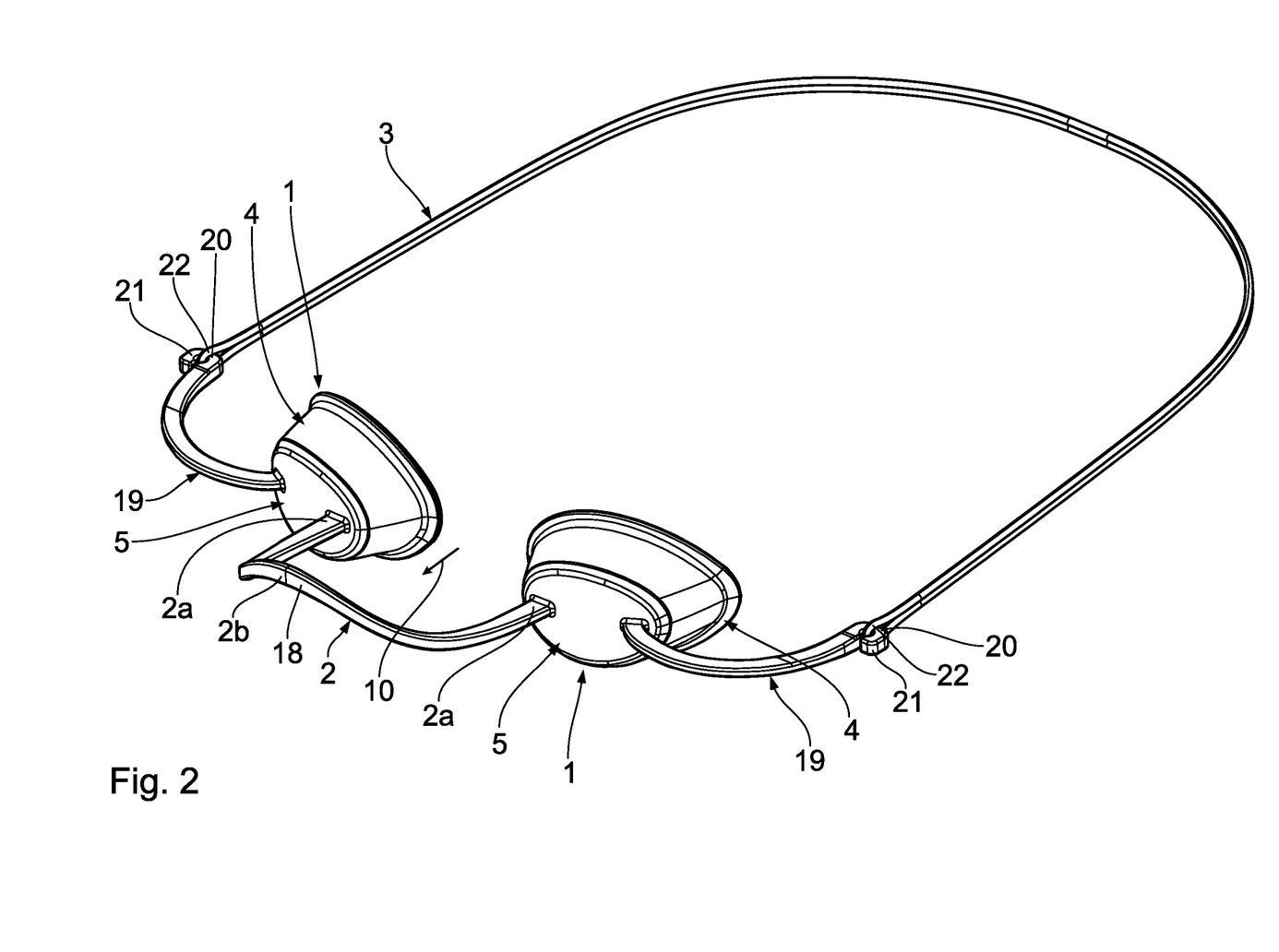
FIG. 2 shows the eye protection goggles according to FIG. 1 in an assembled state.
Figure 3:
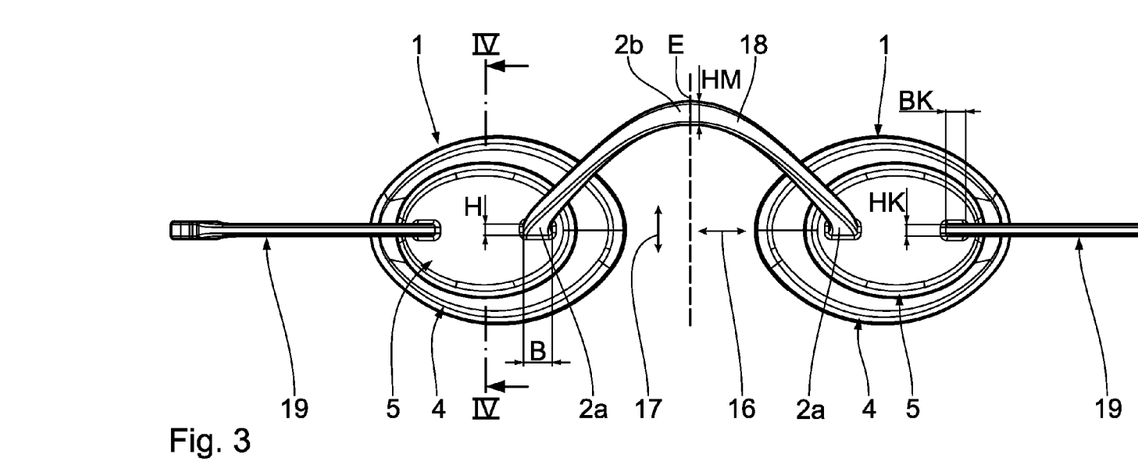
FIG. 3 shows a view from the front, which shows the eye protection caps and a connecting web and the coupling bodies of the eye protection goggles shown in FIGS. 1 and 2.

The connecting web 2 has in principle a uniform cross section. Moving away from the cover protective bodies 5 however the orientation of the cross section of the connecting web 2 changes. Centrally between the cover protective bodies 5 a second cross section 2b of the connecting web 2 is rotated by about 90° relative to the first cross section 2a of the connecting web 2 at the cover protective bodies 5. The connecting web 2 thus has in a central area 18 between the cover protective bodies 5 a height HM in vertical direction 17 and a width BM in width direction 16. This is: $1.2 \leq HM/BM \leq 5$, in particular $1.8 \leq HM/BM \leq 4$. From the cover protective bodies 5 the connecting web 2 runs upwards in its position according to FIGS. 1 to 3 in vertical direction 17.

An arm-like coupling body 19, which is arc-like or curved, is connected to each cover protective body 5. Each coupling body 19 connects to the outer surface 15 in a laterally outer area. From the respective cover protective body 5 each coupling body 19 projects firstly laterally outwardly to the front and then runs in a curve to the rear.

Adjacent to the cover protective bodies 5 each coupling body 19 has a width BK extending in width direction 16 and a height HK extending perpendicular to the latter in vertical direction 17. This is: $1.2 \leq BK/HK \leq 5$, in particular $1.8 \leq BK/HK \leq 4$.

Each coupling body 19 has a holding hook 21 at its free end 20. The headband 3 is mounted detachably in the holding hooks 21 in the assembled state of the eye protection goggles with loops 22 at the ends.

In the following the eye protection goggles are described in more detail in the assembled state.

Figure 4:
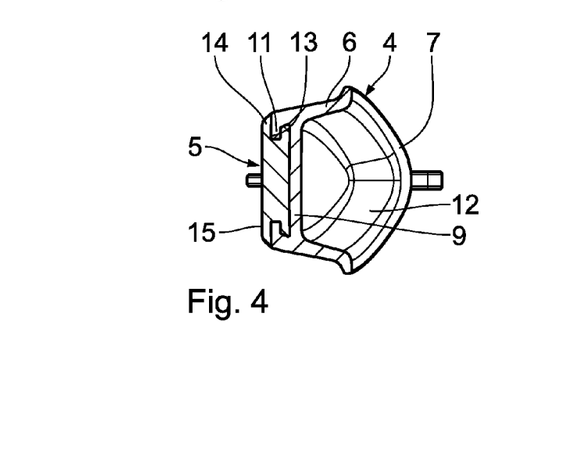
FIG. 4 shows a longitudinal cross section of an eye protection cap according to the section line IV-IV shown in FIG. 3.
Figure 5:
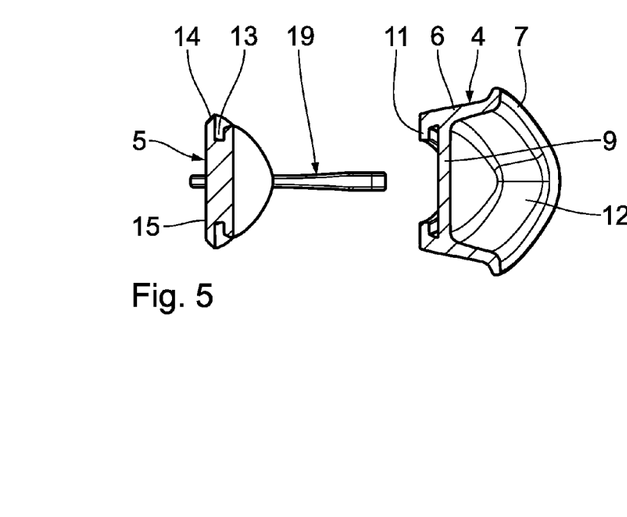
FIG. 5 shows an exploded view of the eye protection cap shown in FIG. 4.

As shown in particular in FIG. 4, in the assembled stated of the eye protection goggles and the eye protection caps 1, the positive locking webs 11 engage externally from the side into complementary positive locking grooves 13, whereby the cover protective bodies 5 are secured locally by positive locking detachably to the basic protective bodies 4. When introducing or inserting the cover protective bodies 5 into the basic protective bodies 4 the positive locking webs 11 snap into the positive locking grooves 13. Each cover protective body 5 then extends parallel and adjacent to the associated cover 9 and also conveniently is placed at least partly, preferably essentially completely, on the latter externally. Each overhang 14 ends essentially externally flush with the respective side wall 6.

To detach the cover protective bodies 5 from the basic protective bodies 4 the positive locking webs 11 are disengaged manually from the positive locking grooves 13.

As already mentioned, the eye protection caps 1 cover the eyes of the person 8 undergoing treatment fully and the inner chambers 12 are open towards the eyes when the eye protection goggles are worn correctly according to FIG. 6. The free edges 7 thus fit closely against the face of the person 8 undergoing treatment.

When the connecting web 2 is folded or pivoted downwards in the vertical direction 17 according to FIG. 6, it is located above or on the nose of the person 8 undergoing treatment so that the forehead area can be treated without any restriction.

Figure 1:
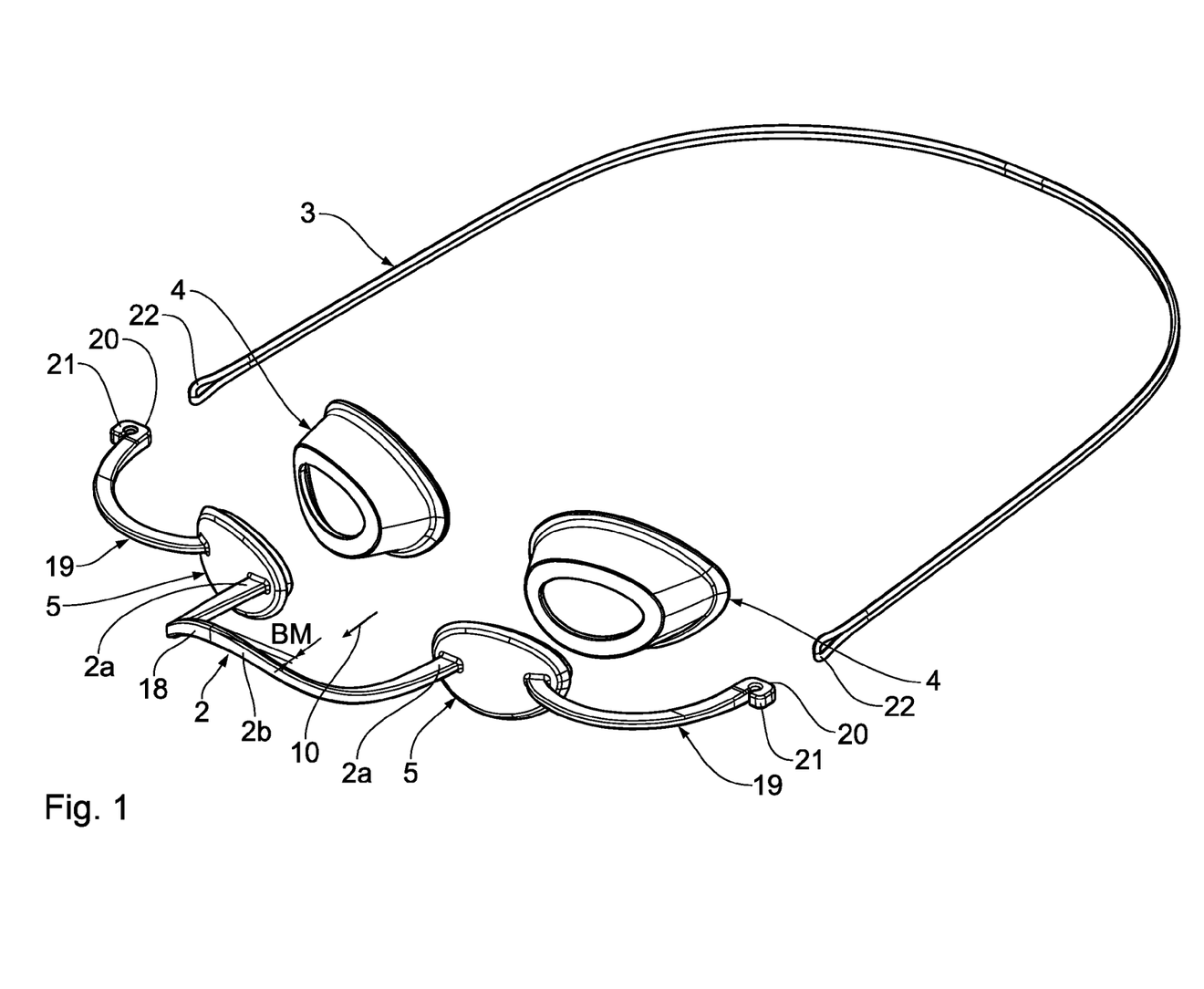
FIG. 1 shows an exploded view of the eye protection goggles according to the invention.

When the connecting web 2 is folded or pivoted upwards in the vertical direction 17 according to FIG. 1, it is located in the forehead area of the person 8 undergoing treatment so that the nose can be treated without any restriction.

The headband 3 runs around the head of the person 8 undergoing treatment so that the eye protection goggles are fixed securely to the head of the person 8 undergoing treatment.

What is claimed is:

1. Eye protection goggles for protecting a person (8) undergoing treatment from electromagnetic radiation, comprising
    two eye protection caps (1), wherein each eye protection cap (1)
        comprises a basic protective body (4) for protecting from electromagnetic radiation, wherein each basic protective body (4) has a free edge (7) configured to be placed on the face of the person (8) undergoing treatment,
        comprises a cover protective body (5) for protecting from frontal electromagnetic radiation, wherein each cover protective body (5) is detachably connected to the respective basic protective body (4), and
        spatially delimits an inner chamber (12), and
    a connecting web (2) connecting the cover protective bodies (5) with each other,
    wherein the cover protective bodies (5) and the connecting web (2) are connected non-detachably in one piece with each other,
    wherein the connecting web (2) comprises at least adjacent to the eye protection caps (1) a first rectangular cross section (2a), extending longitudinally in a width direction (16) of the eye protection goggles, and the connecting web (2) is configured to displace the connecting web (2) relative to the eye protection caps (1) essentially perpendicular to a line of vision (10) of the eye protection goggles in a vertical direction (17) thereof,
    wherein the connecting web (2) has, in the width direction (16) of the eye protection goggles, a width (B) and perpendicular thereto, in a vertical direction (17) of the eye protection goggles, a height (H), wherein $1.2 \leq B/H \leq 5$,
    wherein each basic protective body (4) has an opening defined in an edge opposite to the free edge (7), and wherein each respective cover protective body (5) is detachably connected to the respective basic protective body (4) to close the opening.

2. The eye protection goggles according to claim 1, wherein the basic protective bodies (4) are made from a first material and the cover protective bodies (5) are made from a second material different from the first material.

3. The eye protection goggles according to claim 2, wherein the first material and the second material differ in terms of at least one of hardness and protective effect.

4. The eye protection goggles according to claim 1, wherein the basic protective bodies (4) are flexible.

5. The eye protection goggles according to claim 1, wherein the basic protective bodies (4) are made of silicone.

6. The eye protection goggles according to claim 1, wherein at least one of the cover protective bodies (5) and the connecting web (2) is/are essentially dimensionally stable.

7. The eye protection goggles according to claim 1, wherein at least one of the cover protective bodies (5) and the connecting web (2) is/are essentially dimensionally stable and is/are made from thermoplastic material.

8. The eye protection goggles according to claim 1, wherein at least one of the cover protective bodies (5) and the connecting web (2) is/are essentially dimensionally stable and is/are made from polyoxymethylene.

9. The eye protection goggles according to claim 1, wherein each cover protective body (5) is connected detachably to the associated basic protective body (4) in at least one of a positive locking manner and a force locking manner.

10. The eye protection goggles according to claim 1, wherein each cover protective body (5) comprises at least one positive locking means (13) and each basic protective body (4) comprises at least one counter positive locking means (11) for releasable positive locking with the respective at least one positive locking means (13).

11. The eye protection goggles according to claim 10, wherein the at least one positive locking means (13) is a circumferential groove (13).

12. The eye protection goggles according to claim 10, wherein the at least one positive locking means (13) is a peripheral groove (13).

13. The eye protection goggles according to claim 10, wherein the at least one counter positive locking means (11) is a web (11).

14. The eye protection goggles according to claim 10, wherein the at least one counter positive locking means (11) is a circumferential web (11).

15. The eye protection goggles according to claim 1, wherein the connecting web (2) is displaceable at least partly relative to the eye protection caps (1) essentially perpendicular to the line of vision (10) of the eye protection goggles in the vertical direction (17) thereof.

16. The eye protection goggles according to claim 1, wherein the connecting web (2) spaced apart from the eye protection caps (1) has a second cross section (2b) extending longitudinally in the vertical direction (17) of the eye protection goggles for changing the distance between the eye protection caps (1).

17. The eye protection goggles according to claim 16, wherein the second cross section (2b) is rectangular.

18. The eye protection goggles according to claim 1, wherein the connecting web (2) extends at least partly in the vertical direction (17) of the eye protection goggles and the eye protection goggles is wearable in a first position and a second head position rotated by 180° relative to the first position.

19. The eye protection goggles according to claim 1, wherein on each cover protective body (5) a coupling body (19) for holding a head holding device (3) is arranged.

20. The eye protection goggles according to claim 19, wherein the coupling body (19) projects outwards laterally.

21. The eye protection goggles according to claim 19, wherein the coupling body (19) is arranged for detachably holding a head holding device (3).

22. The eye protection goggles according to claim 19, wherein the coupling body (19) is essentially dimensionally stable.

23. The eye protection goggles according to claim 19, wherein the cover protective bodies (5) and the coupling bodies (19) are joined non-detachably.

24. The eye protection goggles according to claim 19, wherein the cover protective bodies (5) and the coupling bodies (19) are joined forming one piece.

25. The eye protection goggles according to claim 19, wherein each coupling body (19) at least adjacent to the eye protection caps (1) has a third cross section extending longitudinally in the width direction (16) of the eye protection goggles for displacing the coupling bodies (19) relative to the eye protection caps (1) essentially perpendicular to the line of vision (10) of the eye protection goggles in the vertical direction (17) thereof.

26. The eye protection goggles according to claim 25, wherein the third cross section is rectangular.

27. An arrangement as a component of eye protection goggles for protecting a person (8) undergoing treatment from electromagnetic radiation, comprising
    two cover protective bodies (5) which are connectable detachably to two basic protective bodies (4) to form two eye protection caps (1), and
    a connecting web (2) in connection with the cover protective bodies (5),
    wherein the cover protective bodies (5) and the connecting web (2) are connected non-detachably in one piece,
    wherein the connecting web (2) comprises at least adjacent to the eye protection caps (1) a first rectangular cross section (2a), extending longitudinally in a width direction (16) of the eye protection goggles, and the connecting web (2) is configured to displace the connecting web (2) relative to the eye protection caps (1) essentially perpendicular to a line of vision (10) of the eye protection goggles in a vertical direction (17) thereof,
    wherein the connecting web (2) has, in the width direction (16) of the eye protection goggles, a width (B) and perpendicular thereto, in a vertical direction (17) of the eye protection goggles, a height (H), wherein 1.2≤B/H≤5,
    wherein each basic protective body (4) has an opening defined in an edge opposite to the free edge (7), and wherein each respective cover protective body (5) is detachably connected to the respective basic protective body (4) to close the opening.

* * * * *